United States Patent [19]

Play et al.

[11] Patent Number: 4,511,653
[45] Date of Patent: Apr. 16, 1985

[54] PROCESS FOR THE INDUSTRIAL PREPARATION OF COLLAGENOUS MATERIALS FROM HUMAN PLACENTAL TISSUES, HUMAN COLLAGENOUS MATERIALS OBTAINED AND THEIR APPLICATION AS BIOMATERIALS

[75] Inventors: Dominique Play; Marc Bonneau; Charles Merieux; Daniel Herbage, all of Lyons; Philippe Comte, Sainte-Foy-Les-Lyon, all of France

[73] Assignees: Foundation Merieux; Centre Technique du Cuir, both of Lyons, France

[21] Appl. No.: 545,398

[22] PCT Filed: Nov. 25, 1982

[86] PCT No.: PCT/FR82/00199

§ 371 Date: Oct. 14, 1983

§ 102(e) Date: Oct. 14, 1983

[30] Foreign Application Priority Data

Nov. 26, 1981 [FR] France ............................... 81 22606

[51] Int. Cl.³ ......................... C08H 1/06; C12P 21/06
[52] U.S. Cl. .................................. 435/69; 260/123.7; 128/334 R; 422/243; 435/41; 514/21; 514/801
[58] Field of Search ........................ 260/123.7; 435/69

[56] References Cited

U.S. PATENT DOCUMENTS

| 3,314,861 | 4/1967 | Fujii .................................. 435/69 |
| 3,637,642 | 1/1972 | Fujii .............................. 260/123.7 X |
| 3,738,913 | 6/1973 | Johnsen et al. ...................... 435/69 |
| 4,021,522 | 5/1977 | Daniel ........................... 260/123.7 X |
| 4,097,234 | 6/1978 | Sohde et al. .................... 260/123.7 X |
| 4,140,537 | 2/1979 | Luck et al. ..................... 260/123.7 X |
| 4,210,721 | 7/1980 | Monsheimer et al. ................. 435/69 |
| 4,285,986 | 1/1980 | Cioca et al. .................... 260/123.7 X |
| 4,293,647 | 10/1981 | Monsheimer et al. ................. 435/69 |

OTHER PUBLICATIONS

Die Angewandte Makromolekulare Chemie, Band 82, No. 1276, Nov. 1979, Riemschneider et al., pp. 171-186.
Chem. Abstracts, vol. 83, No. 5, 1975, 39071n, Henkel et al.
Biochemistry, vol. 18, No. 14, Jul. 1979, pp. 3089-3097, Kresina et al.
Chem. Abstracts, vol. 68, 1968, 9425d, Stainsby et al.
Hoppe-Seyler's Z. Physiol. Chem., Bd. 356, S. 567-575, May 1975, Henkel, Isolierung und Eigenschaften eines nach Alaki-Vorbehandlung loeslichen Arterienkollagens.

*Primary Examiner*—Howard E. Schain
*Attorney, Agent, or Firm*—Karl F. Ross; Herbert Dubno

[57] ABSTRACT

This process of preparation consists in subjecting said placental tissue after pressing, grinding and washing in a neutral and acid medium to a treatment in alkaline medium at a temperature less than or equal to 10° C. and in then subjecting the portions of collagen solubilized during this treatment, as well as the collagen solutions resulting from an eventual subsequent treatment for the solubilization, at least partial, of the insoluble residue, to purification by chromatography on an anion exchange resin, at a temperature less than or equal to 10° C., followed with fractional precipitation of the collagens by salts in acid medium.

The human collagenous materials obtained can be used as biomaterials in biotechnology and in pharmacy and are perfectly immunologically innocuous for the human species.

5 Claims, No Drawings

PROCESS FOR THE INDUSTRIAL PREPARATION OF COLLAGENOUS MATERIALS FROM HUMAN PLACENTAL TISSUES, HUMAN COLLAGENOUS MATERIALS OBTAINED AND THEIR APPLICATION AS BIOMATERIALS

This invention relates to a process for the industrial preparation of new insoluble and soluble collagenous materials from human placental tissues as well as to the human collagenous materials obtained and their application as biomaterials.

Collagens are the main proteinic constituents of conjunctive tissue such as the dermis, cartilage, tendons, vascular walls... to which they impart the mechanical properties essential to their physiological functions. At the present time, at least five main types of collagen have been isolated and characterized. They can be classified into two main groups: collagens of types I, II and III present in tissues as fibers and often termed interstitial collagens and collagens of types IV and V termed basal membrane collagens whose molecular composition and form within the tissues are still imperfectly known.

These collagens, although different with regard to their primary sequence, have a common triple helix tertiary structure which protects them against degradation by proteolytic enzymes other than collagenases.

After their intracellular synthesis, collagens are excreted in soluble form into the extracellular medium where they aggregate to form fibrils. During maturation of the tissues, these fibrils become rapidly insolubilized as a result of crosslinking of the collagen molecules through formation of interchain covalent bonds. These bonds form at the extremity of at least one of the molecules in a non helicoidal region and therefore in a region which may be cleaved by the action of proteolytic enzymes.

Two types of processes make it possible, at present, to extract substantial quantities of collagens from a tissue.

One of these processes uses tissues obtained from young mammals in which there is a substantial fraction of non crosslinked collagen and uses the solubility properties of these collagens in neutral saline solutions or in dilute acids as described, for example, in French Pat. Nos. 1 568 829 and 1 596 789 in which soluble collagen is prepared from calf skins.

These extraction processes have, however, several drawbacks: on the one hand, they require the use of animal tissues only as a base material and, on the other hand, they provide collagen of type I only.

Other types of processes use mature tissues; it then becomes indispensable to use the proteolytic activity of enzymes such as pepsin, pronase or trypsin to cut down the telopeptides of the collagens not protected by the triple helix and thus break the intermolecular bonds responsible for their insolubility.

In human tissues, the placental tissue alone is available in sufficient quantities to eventually provide for a separation of human collagens on an industrial scale.

The difficulties encountered in the preparation of purified collagens from this tissue are numerous and result essentially from:

the low collagen content of the starting tissue (10 to 15%)

the insolubility of these collagens the possible presence of hepatitis viruses in the starting material.

It has been proposed to treat this tissue with neutral or acidic saline solutions (NaCl) (German patent application DAS No. 26 16 939) or with concentrated urea solutions (German patent application OS No. 24 62 221) in order to extract therefrom the soluble part present in low concentration. Various studies carried out in the laboratory have improved this collagen extraction from placental tissue by partial digestion with pepsin of 20 to 40% of the starting collagens (see, in particular, BIOCHEMISTRY, vol. 18, no. 14—July 10, 1979—T. F. Kresina—p. 3091) and fractionation thereof into collagens of types I, III, IV and V. The main drawbacks of these methods are as follows:

enzymatic digestion of the total tissue requires the treatment of substantial weights and volumes of tissue and extracts as well as the use of large quantities of enzymes. Indeed, the proteolytic enzyme acts at this level not only on collagen telopeptides but also on the non collagenous protein mass (60% of the starting dry weight), it is possible to extract only 20 to 40% of the total collagen and the extracts have a very low collagen concentration, hepatitis viruses generally contaminate the different fractions extracted and therefore prevent the use of the products as biomaterials. It then becomes necessary to start with placental tissues that have been previously selected by means of an immunological method and which are free of this viral contaminant.

It has been further proposed (Die angewandte Makromolekulare Chemie, vol. 82 no. 1276, 1979, p. 174, table 1) to pretreat cow placentas with a dilute solution of sodium hydroxide or sodium acetate (0.1M); this pretreatment in such a weakly alkaline medium, however, provides for the extraction, after 24 hours, of only 0.5% of collagen; furthermore, it does not increase the subsequent proportion of solubilization of the collagen through the action of pepsin, which proportion remains at approximately 30%.

This invention aims at correcting these drawbacks by proposing a process for the industrial treatment of human placental tissues which makes it possible to obtain new insolubles collagenous materials as well as soluble collagens of different types, in particular, free of viral contamination.

This process is original in that:

it starts from batches of human placental tissues which may even be contaminated by hepatitis viruses;

it solubilizes up to 40% of the total collagen without the necessity of using proteolytic enzymes;

it solubilizes almost all of the collagen by enzymatic attack using very low quantities of a wide range of proteolytic enzymes;

it provides slightly modified collagens (deamination and elimination of part of the telopeptides), by maintaining their biological properties;

it provides for the preparation of a practically pure insoluble collagenous material which can be used as a support for cultures of different types of cells;

all the compounds obtained are free of viral contamination and can be used as biomaterials.

The steps in the process according to the invention will now be described in detail:

The preparation of the placental tissues (whether these involve fresh tissues or the final residue of the treated tissues with a view to the preparation of therapeutic gamma-globulins and albumin) consists of a succession of pressing, grinding and washing operations in neutral and acid medium. This material is then subjected to a first alkaline treatment, for example, with 0.5M sodium hydroxide or saturated limewater solutions for variable times at temperatures not exceeding 10° C. This first treatment is essential for several reasons:

It eliminates the major part of the non collagenous compounds which are solubilized;

It is a first inactivation step for hepatitis viruses;

It solubilizes directly 10 to 20% of the collagen which might be purified using the general method described below (extract 1);

It facilitates the subsequent solubilization of the insoluble collagen with or without the use of proteolytic enzymes;

It provides an insoluble residue A which is equivalent to only 20% by weight of the dry starting material but which contains over 70% collagen ($>80\%$ of the starting collagen).

From this residue A, it is subsequently possible to prepare an insoluble collagenous material and to solubilize 20 to 35% of the total collagen without the use of proteolytic enzymes.

For this purpose, residue A is treated in succession with a second alkaline solution (for example, a 0.1 to 0.5M sodium hydroxide solution at 4° C. for 12 to 48 hours) (extract 2) and then with a dilute acid solution (for example, acetic acid (0.1 to 0.5M) (acid extract) at 4° C. for 5 to 12 hours). The residue is termed Residue B.

This treatment of residue A has several advantages:
complete inactivation of hepatitis viruses;
preparation of a collagen purified insoluble material (residue B) (collagen content $>85\%$) and corresponding to 50–70% of the starting collagen;
solubilization of 20 to 35% of the total collagen without enzymes.

These collagens are concentrated in the second alkaline extract (60–70% of collagen) and in the acid extract (75–85% of collagen), which facilitates their final purification.

It is also possible to solubilize almost all of the collagens present from residue A.

Residue A is subjected to partial enzymatic digestion by proteolytic enzymes such as pepsin, pronase, papain and trypsin. Due to the fact that the non helicoidal extremities are made fragile by the first alkaline treatment, the collagens are entirely solubilized. The already collagen purified extract (70–80%) can then be subjected to the fractionation developed for the different extracts.

The purification and fractionation of the collagens present in the different extracts (alkaline extracts no. 1 and 2, acid extract and enzymatic extract) are carried out according to the following general procedure: the first step comprises chromatography on an anion exchange resin of the DEAE type, on an industrial scale at a temperature not exceeding 10° C. Collagens in the native state are not held back on the column whereas the contaminating acid glycoproteins and proteoglycans remain on the column. Furthermore, in the case of alkaline extract no. 1 which still contains hepatitis viruses which may not have been destroyed, this chromatography makes it possible to separate the collagens from the viral contaminants.

The second step comprises the fractional precipitation of collagens by salts in acid medium. Thus, the collagen fraction not held back on the DEAE-Spherosil column is concentrated and then passed in an acid medium (0.1M acetic acid). By gradual addition of neutral salts (example, NaCl) collagens of Types I and III are precipitated in 0.7M NaCl followed by collagens of types IV and V in 1.2M NaCl. If the final separation of these two groups of collagens is necessary, it is then possible to use conventional methods: for collagens of types I and III, chromatogrphy on DEAE-Spherosil with increasing ionic force gradient elution and for collagens of types IV and V, precipitation of type V with a 0.02M $Na_2HPO_4$ solution. The type IV collagen remains in solution.

The collagens extracted from the placenta using the process described in this disclosure are chemically different from the collagens extracted by pepsic attack of the whole placenta. Indeed, alkaline treatment induces a partial deamination (20 to 30%) of asparagin and glutamine which gives rise to a larger negative charge. The solubility of these collagens in neutral medium is improved. Their molecular sizes and their helicoidal structure are not modified but their capacity to form fibrils again in vitro is decreased just as with collagens subjected to the action of pepsin. Their biological properties, however, are not altered which makes it possible to use them as biomaterials as described below.

This invention will now be illustrated by the following non limiting examples.

EXAMPLE 1

Freshly removed and frozen human placentas (160 kg—humid), transported at $-20°$ C. and thawed out by passing them on a heating screw, were ground and pressed so as to separate the interstitial blood from the placental tissue. The tissue was then washed in a 9% NaCl solution containing ethanol (3%) in the proportion of four volumes of solution to 1 volume of tissue so as to eliminate as much bloody liquid and hemoglobin as possible.

The residual tissue (80 kg—humid, containing 14% dry material, or 11.2 kg, 14.8% of which was collagen or 1.65 kg) was considered as the starting material for the calculation of the extraction ratios. It was subjected to a first alkaline treatment with $2 \times 400$ liters of 0.5M NaOH solution at 4° C. for 48 hours. After centrifugation for 30 mn at 2000 g, the alkaline extract (no. 1) containing 15% of starting collagen was either eliminated, or subjected to the purification scheme for the collagens described in example no. 2. The residue from alkaline treatment no. 1 (20 kg—humid) was termed residue A. It contained 17% of the starting dry weight or 1.9 kg and 82% of the starting collagen (1.35 kg), the collagen content thereof being indeed 71%.

This residue A was subjected to a second alkaline treatment (100 liters of 0.5M NaOH) for 48 hours at 4° C. After centrifugation, alkaline extract no. 2 (0.4 kg), which contained 16% of the total collagen, could either be eliminated or treated according to the procedure described in example no. 2. The residue of this second alkaline treatment was extracted with $2 \times 80$ liters of a 0.5M acetic acid solution for 12 hours at 10° C. This acid extract contained 5% of the total collagen (0.08 kg). The final residue, termed residue B, was washed with distilled water and then preserved frozen or freeze-dried depending on the projected use. It corresponded to 12% of the dry starting weight (1.34 kg) and to 68% of the collagen (1.13 kg). Its collagen content was indeed 85%.

EXAMPLE 2

20 kg of residue A (residue of the first alkaline treatment of placental tissue) and containing 1.9 kg of dry material, 1.35 kg of which was collagen, were placed in 100 liters of 0.5M acetic acid containing 100 g of pepsin (Organotechnie, Type 700, 10000 NS). After incubation for 24 hours at 10° C., the insoluble residue (less than 10% of residue A) was eliminated by centrifugation. The pepsic extract was concentrated by ultrafiltration on a Millipore membrane (PTGC 1000) and then taken up again and equilibrated with a 0.1M, pH 6.8 phosphate buffer.

This solution was chromatographed on a 50 cm/100 cm Pharmacia column packed with a DEAE-Spherosil resin at an elution rate of 10 l/hour. The non-retained fraction (80 l) which contained the collagens was then concentrated again and equilibrated in 50 liters of 0.5M acetic acid by ultrafiltration. Increasing quantities of NaCl were added to this solution and coprecipitation occurred for collagens of Types I and III (720 g) at a NaCl concentration of 0.7M and for collagens of Types IV and V (50 g) at a NaCl concentration of 1.2M. In order to improve purification, successive redissolutions and saline reprecipitations can be carried out.

This process of purification (chromatography on DEAE-Spherosil +saline precipitations) can be used for collagens extracted according to example 1 without enzymatic digestion and contained in alkaline extracts no. 1 and no. 2 and the acid extract.

The immunological determination by radioimmunoassay of viral antigenicity in the different residues and extracts of these two examples shows that:

after two alkaline treatments, the viral antigen had completely disappeared;

after a single alkaline treatment, antigenicity was attenuated but was still present. It was then totally eliminated from the extracted collagens by chromatography on DEAE-Spherosil.

The invention also relates to industrial applications, in particular, in the fiels of biotechnology and pharmacy, of the various human placental collagen preparations obtained through the use of the process according to the invention.

APPLICATIONS IN BIOTECHNOLOGY (a) Cell cultures:

The collagens obtained according to the invention can be used as in vitro culture supports for various differentiated cellular species and types.

The following cell culture can be mentioned as a non limiting example:

The insoluble collagens (residue B of example 1) obtained from the alkaline extractions (steps 1 and 2) and consisting of the mixtures of types I, III, V were textured as a film and deposited on the bottom of different tissue culture containers such as tanks, flasks, Petri dishes, etc. Similarly, the soluble placental collagens of different types obtained using the process according to the invention could be deposited with or without cross-linking at the surface of various containers (flasks, dishes, cover-glasses, etc.) or materials (glass beads, etc.) and act as culture supports for various cellular types. The containers containing the layer of collagen were then sterilized either with heat (110° C. in an autoclave for 40 mn) or by radiation ($\gamma$ or ultraviolet rays). It was then possible to proceed to the culture of hepatocytes as follows: sterile surgical exeresis of a monkey liver fragment was effected. The sample was sectioned into small fragments having a diameter of 5 mm, placed in Eagle medium and then dissociated by scraping between two sterile cover-glasses. The cell suspension obtained was counted by dilution-counting in a Thoma cell under the microscope and then adjusted to $10^7$ cells/ml in Eagle medium to which had been added 10% of fetal calf serum. 10 ml ($100 \times 10^6$ cells) of the cell suspension were then deposited on the collagen film contained in a 250 ml flask and 90 ml of Eagle medium, to which had been added 10% of fetal calf serum, were then added. The closed flask was placed in a 37° C. oven for 24 hours. The supernatant liquid was then discarded and replaced with 100 ml of fresh medium (Eagle +20% of fetal calf serum). The flask was replaced at 37° C. for several days. Under these conditions, the differentiated hepatocyte culture on a bed of collagen could be observed for over 10 days. This differentiated hepatocyte culture can provide a support for the replication and multiplication of human hepatitis viruses for the purpose of subsequent production of a vaccine.

The cultures of the various differentiated cells such as lymphocytes, macrophages, chondrocytes, endotheliocites, nerve cells, gland cells can also be obtained on a layer of human placental collagen.

(b) Culture of embryos:

Petri dishes covered with an insoluble collagen gel can receive fertilized mammal ovocytes cultivated in Ham medium. The collagen support facilitates better nidation and improved and prolonged segmentation of the ovocyte beyond the blastocyte stage. This advanced embryonic culture provides increased observation, analysis and selection of the embryo before its transfer into the uterus.

(c) Tissue or organ culture:

The culture of differentiated tissue or organ fragments (skin, thyroid and adrenal glands, pancreas, etc.) can also be obtained on human placental collagen supports provided according to the invention.

(d) Production of equipment and apparatus to be used in biological and medical engineering and in industrial engineering:

The collagens obtained according to the invention can be used, for example, for the production of equipment for therapeutic cleansing or human plasma or blood complementation applications (dialysis, artificial pancreas, etc.). Thus, they can be used as membranes which can be mounted in parallel in a module designed for extracorporal dialysis in man. The membranes can be pretreated before mounting, for example, by grafting or inclusion into or onto the collagen material of active biological molecules: antibodies, antigens, enzymes, hormones, etc., so as to present a specificity of immunological, enzymatic or hormonal action which will show up during dialysis, cleansing or therapeutic complementation by extracorporal blood circulation in man.

Similarly, the collagens obtained according to the invention and included as membranes in industrial filtration, dialysis or fractionation apparatus make it possible to obtain high resolution industrial separations of complex biological liquids by affinity chromatography.

PRODUCTION OF PROSTHETIC DEVICES AND BIOMATERIALS FOR PHARMACEUTICAL USE (a) Insoluble collagens:

The insoluble collagens according to the invention can be used in the production of hemostatic sponges or can also be textured as suture threads or membranes for surgical use.

The insoluble collagens obtained according to the invention can be textured as films which can receive, by codeposition, adsorption, mechanical inclusion or grafting, all biologically active compounds such as enzymes, hormones, antigens, antibodies, vitamins and growth factors; these collagen films thus activated constitute biologically active prosthetic devices which can be implanted with permanent therapeutic effects and which are well suited for a certain number of human affections.

(b) Soluble collagens:

The soluble collagens prepared as biodegradable microfibrils can be used either alone in post-traumatic complementation therapy or in combination with human hemoglobin with a view, for example, to the production of biodegradable homologous synthetic blood.

The prosthetic devices and biomaterials prepared from the different types of human collagens of placental origin, either alone or in association, obtained according to the invention, are free of any noteworthy antigenicity for the human species. They are therefore well tolerated and represent a new generation of biomaterials for human medicine.

We claim:

1. A process for the industrial preparation of human collagenous material from human placental tissue which comprises the steps of:
   (a) pressing, grinding, and washing said placental tissue in a neutral or acid medium;
   (b) subjecting the placental tissue treated according to step (a) to an alkaline treatment with a 0.5M NaOH, a 0.5M KOH, or a saturated lime water solution at a temperature less than or equal to 10° C.;
   (c) centrifuging the placental tissue treated according to step (b) to form a first alkaline extract containing 10 to 20% by weight of the collagen in the placental tissue and to form a first insoluble residue which is equivalent to only 20% by weight of the placental tissue but which contains over 80% of the collagen in the placental tissue;
   (d) removing the first alkaline extract from the first insoluble residue;
   (e) treating the first insoluble residue formed during step (c) with a 0.1 to 0.5M NaOH solution at a temperature less than 10° C.;
   (f) centrifuging the insoluble residue treated according to step (e) to form a second alkaline extract which contains about 16% of the collagen in the placental tissue;
   (g) removing the second alkali extract from the first insoluble residue; and
   (h) extracting the first insoluble residue subsequent to step (g) with a 0.1 to 0.5M acetic acid solution at a temperature less than 10° C. to form a second insoluble residue having a collagen content of about 85% and corresponding to about 68% by weight of the collagen in the placental tissue and an acid extract containing about 5% by weight of the collagen in the placental tissue, and removing the acid extract.

2. The process defined in claim 1 wherein the first alkaline extract removed during step (d) is then chromatographed on an anion exchange resin, at a temperature less than or equal to 10° C., followed by fractional precipitation of the collagen by salts in an acid medium.

3. The process defined in claim 1 wherein the second alkaline extract removed during step (g) is then chromatographed on an anion exchange resin, at a temperature less than or equal to 10° C., followed by fractional precipitation of the collagen by salts in an acid medium.

4. A process for the industrial preparation of human collagenous materials from human placental tissue which comprises the steps of:
   (a) pressing, grinding and washing said placental tissue in a neutral or acid medium;
   (b) subjecting the placental tissue treated according to step (a) to an alkaline treatment with a 0.5M NaOH, a 0.5M KOH, or a saturated lime water solution at a temperature less than or equal to 10° C.;
   (c) centrifuging the placental tissue treated according to step (b) to form an alkaline extract containing 10 to 20% by weight of the collagen in the placental tissue and to form an insoluble residue which is equivalent to only 20% by weight of the placental tissue but which contains over 80% of the collagen in the placental tissue;
   (d) removing the alkaline extract from the insoluble residue;
   (e) subjecting the insoluble residue formed during step (c) to partial enzymatic digestion with a proteolytic enzyme selected from the group consisting of pepsin, pronase, papain, and trypsin to solubilize the collagen; and
   (f) chromatographing the solubilized collagen on an anion exchange resin at a temperature less than or equal to 10° C., followed by fractional precipitation of the collagen by salts in an acidic medium.

5. The process defined in claim 4, wherein the alkali extract removed during step (d) is subjected to chromatographing on an anion exchange resin at a temperature less than or equal to 10° C., followed by fractional precipitation of the collagen using salts in an acid medium.

* * * * *